United States Patent [19]

Simmons

[11] Patent Number: 4,596,597

[45] Date of Patent: Jun. 24, 1986

[54] ESTERS OF 1,2 AND 3-N,N-DIALKYLCARBAMYL-5-SUBSTITUTED-1H-1,2,3-TRIAZOLE-4-CARBOXYLIC ACID

[75] Inventor: Kirk A. Simmons, Langhorne, Pa.

[73] Assignee: Stauffer Chemical Company, Westport, Conn.

[21] Appl. No.: 747,465

[22] Filed: Jun. 21, 1985

[51] Int. Cl.[4] .................. A01N 43/647; C07D 249/04; C07D 249/06; C07D 403/06; C07D 401/06

[52] U.S. Cl. ........................................ 71/92; 546/210; 548/255

[58] Field of Search ............... 546/210; 548/255; 71/92

[56] References Cited

U.S. PATENT DOCUMENTS 4,233,059  11/1980  Krüger et al. ............... 548/255

Primary Examiner—Robert T. Bond
Attorney, Agent, or Firm—Edwin H. Baker

[57] ABSTRACT

A compound having the structural formula

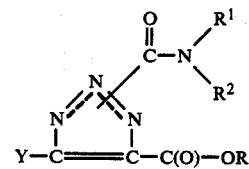

wherein Y is hydrogen, bromine, phenyl or $C_1$–$C_4$ alkyl; R is $C_1$–$C_{10}$ alkyl, $R^1$ and $R^2$ independently are $C_1$–$C_6$ alkyl or $R^1$ and $R^2$ together form a ring with the nitrogen to which they are attached having 3-8 carbon atoms, optionally substituted with one or two methyl groups.

20 Claims, No Drawings

ESTERS OF 1,2 AND 3-N,N-DIALKYLCARBAMYL-5-SUBSTITUTED-1H-1,2,3-TRIAZOLE-4-CARBOXYLIC ACID

BACKGROUND OF THE INVENTION

Compounds of the formula shown below wherein R is 2-benzothiazolyl,

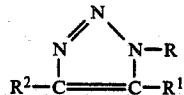

2-benzimidazolyl, 2-benzoxazolyl, s-triazinyl or 4-pyrimidinyl and $R^1$ and $R^2$ are hydrogen, hydroxyalkyl, carbomethoxy, alkyl, $(CH_2)_3$, $(CH_2)_4$, or $(CH_2)_5$ are described by Auderhaar and Meyer in Ger. Offen. No. 2,263,878 as being pesticidal.

DESCRIPTION OF THE INVENTION

This invention relates to esters of 1, 2 and 3-N,N-dialkylcarbamyl-5-(H, Br, alkyl or phenyl)-1H-1,2,3-triazole-4-carboxylic acid as herbicides. The novel compounds of this invention have the following structural formula (A)

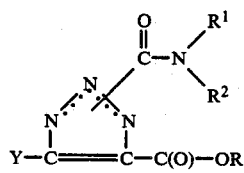

wherein

Y is hydrogen, bromine, phenyl or $C_1$–$C_4$ alkyl;

R is $C_1$–$C_{10}$ alkyl, preferably $C_3$–$C_6$ alkyl, more preferably $C_3$–$C_5$ alkyl, most preferably isopropyl, isobutyl, isopentyl, or sec-pentyl;

$R^1$ and $R^2$ independently are $C_1$–$C_6$ alkyl, preferably $C_1$–$C_4$ alkyl, or $R^1$ and $R^2$ together form a ring with the nitrogen to which they are attached, having 3–8 carbon atoms, optionally substituted with one or two methyl groups.

Structural formula A is intended to define compounds of either of the following three structural isomers:

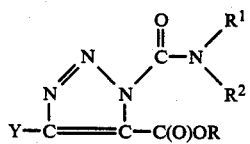
3-isomer

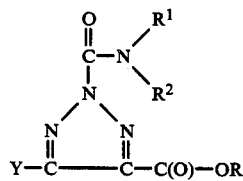
2-isomer

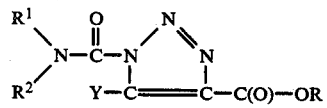
1-isomer or mixtures of the three isomers in any proportion.

All three isomers are herbicidally active.

In the above description of the compounds of this invention alkyl includes both straight and branched configurations; for example, methyl, ethyl, n-propyl, isopropyl, n-butyl, sec-butyl, isobutyl, and tert-butyl, the amyls, the hexyls, the heptyls, the nonyls and the decyls.

The compounds of this invention are active herbicides of a general type. That is, they are herbicidally effective against a wide range of plant species. The method of controlling undesirable vegetation of the present invention comprises applying an herbicidally effective amount of the above-described compounds to the area where control is desired.

The compounds of the present invention can be prepared by the following general method.

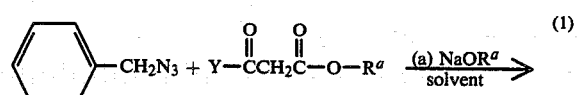
(1)

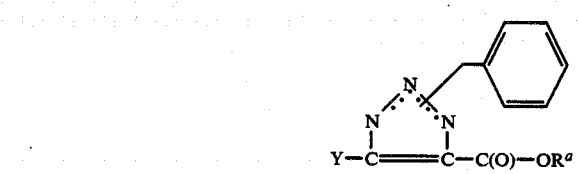

wherein Y is as defined and $R^a$ is $C_1$–$C_4$ alkyl.

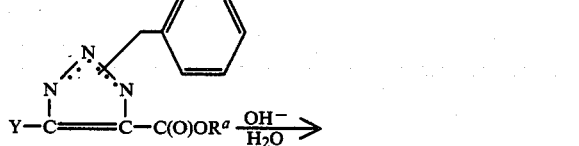
(2)

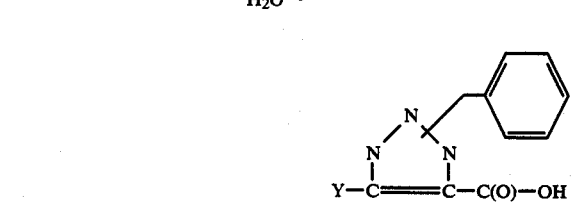

wherein Y and $R^a$ are as defined.

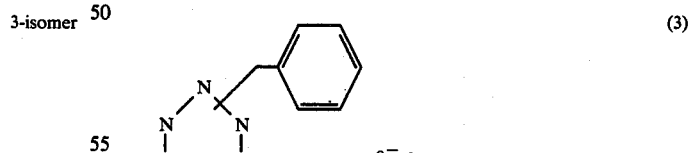
(3)

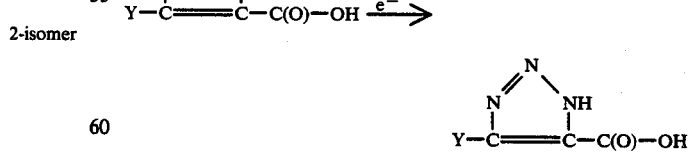

wherein Y is as defined.

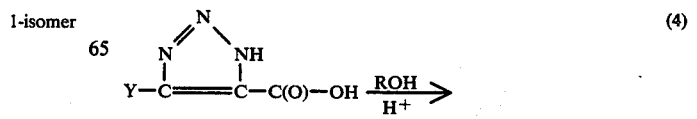
(4)

-continued

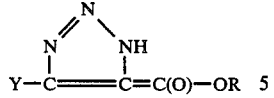

wherein Y and R are as defined.

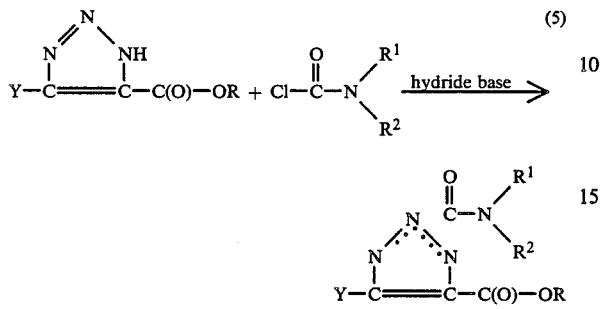

wherein Y, R, $R^1$ and $R^2$ are as defined.

Generally, step (1) is run in solvent such as ethanol using a base, preferably sodium ethoxide. The ketoacetate and azide reactants are used in equimolar amounts and the base is used in a 1.5 to 2-fold excess.

Reaction step (2) is run using a hydroxide base such as sodium hydroxide in a 1.5 to 2-fold excess.

Reaction step (3) is run in liquid ammonia at −78° C. with a mole amount of sodium metal. If water is present, an excess of ammonia should be used.

Reaction step (4) is run in a 10-fold excess of anhydrous alcohol at reflux temperature. The acid catalyst used in preferably hydrogen chloride gas.

Reaction step (5) is run in an organic solvent such as tetrahydrofuran, at a temperature of about 25°–100° C., preferably reflux temperature, using equal mole amounts of the two reactants and a hydride base. Preferably, the hydride base is sodium hydride. Organic bases can also be used.

The reaction product is a mixture of (1), (2) and (3) isomers and is worked up by conventional techniques.

The following examples teach the synthesis of representative compounds of this invention.

EXAMPLE 1

1(2 or 3)-Benzyl-5-ethyl-1H-1,2,3-triazole-4-carboxylic acid

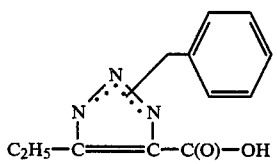

To a solution of 4.3 grams (g) (187 mmoles) of sodium pellets in 80 milliliters (ml) of absolute ethanol under nitrogen was added 18.0 g (125 mmoles) of ethyl propionyl acetate followed by 16.6 g (125 mmoles) of benzyl azide. The resulting reaction mixture was stirred under reflux for two days. Upon cooling to room temperature, 45 ml of 4N aqueous sodium hydroxide was added dropwise and the mixture was refluxed for 3 hours. The reaction was again cooled to room temperature and concentration in vacu gave a gummy solid. This residue was dissolved in 125 ml of water and extracted with ether. Acidification (pH 1) with 12 molar hydrochloric acid caused precipitation of 25.1 g (87%) of 1(2 or 3)-benzyl-5-ethyl-1H-1,2,3-triazole-4-carboxylic acid as a tan solid. The structure was confirmed by nuclear magnetic resonance (n.m.r.) and infrared spectroscopy (I.R.).

EXAMPLE 2

5-Ethyl-1H-1,2,3-triazole-4-carboxylic acid

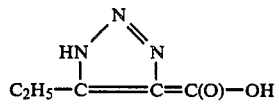

To a mixture of 24 g (104 mmoles) of 1(2 or 3)-benzyl-5-ethyl-1H-1,2,3-triazole-4-carboxylic acid in 250 ml of liquid ammonia at −78° C., 7.2 g (312 mmoles) of sodium pellets were added, in portions, until the solution maintained a dark blue color. The reaction was then quenched with 10 g (128 mmoles) of ammonium carbonate. The resulting yellow mixture was allowed to warm to room tempreture and the ammonia evaporated. The solid residue was dissolved in 70 ml of water and extracted with ether. The aqueous phase was then adjusted to pH 1 with 12 molar hydrochloric acid and 14.0 g (95%) of 5-ethyl-1H-1,2,3-triazole-4-carboxylic acid was precipitated as a yellow solid. The stucture was confirmed by n.m.r. and I.R.

EXAMPLE 3

Isopropyl of 5-Ethyl-1H-1,2,3-triazole-4-carboxylate

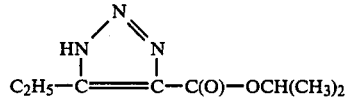

A mixture of 10 g (73.5 mmoles) of 5-ethyl-1H-1,2,3-triazole-4-carboxylic acid and 100 ml of anhydrous isopropyl alcohol was saturated with hydrogen chloride gas and heated to reflux overnight. The cooled reaction mixture was then concentrated in vacuo to give a yellow oil. To this residue was added 15 ml of water and 13.4 g (100%) of isopropyl 5-ethyl-1H-1,2,3-triazole-4-carboxylate precipitated as a tan solid. The structure was confirmed by n.m.r. and I.R.

EXAMPLE 4

Isopropyl 1(2 and 3)-N,N-dimethylcarbamyl-5-ethyl-1H-1,2,3-triazole-4-carboxylate

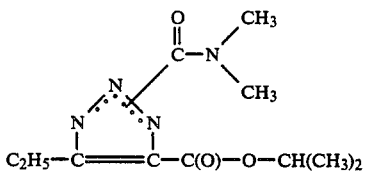

To a suspension of 393 milligrams (mg) (16.4 mmoles) of sodium hydride in anhydrous tetrahydrofuran was added 3 g (16.4 mmoles) of isopropyl 5-ethyl-1H-1,2,3-triazole-4-carboxylate in portions. The resulting suspension was cooled to 0° C. and 1.75 g (16.4 mmoles) of dimethylcarbamyl chloride was added dropwise. The reaction mixture was filtered to remove the precipitated sodium chloride and concentration of the filtrate in vacuo gave 4.0 g (96%) of isopropyl 1(2 or 3)-N,N-dimethylcarbamyl-5-ethyl-1H-1,2,3-triazole-4-carboxylate as a golden oil. The structure was confirmed by n.m.r. and I.R.

The following is a table of certain selected compounds that are preparable according to the procedure described herein. Compound numbers assigned to each compound are used throughout the remainder of the application.

TABLE I $$\underset{Y-C=\!\!=\!\!C-C(O)-OR}{\overset{N\diagdown \diagup N}{\underset{N}{\,}}}\!\!-\!\!\overset{O}{\overset{\|}{C}}\!\!-\!\!N\!\!\diagup\!\!\overset{R^1}{\diagdown R^2}$$

| Compound Number | R | Y | $R^1$ | $R^2$ |
|---|---|---|---|---|
| 1 | $CH_3$ | $C_2H_5$ | $CH_3$ | $CH_3$ |
| 2 | $CH_3$ | $i\text{-}C_3H_7$ | $CH_3$ | $CH_3$ |
| 3 | $i\text{-}C_3H_7$ | $CH_3$ | $CH_3$ | $CH_3$ |
| 4 | $i\text{-}C_3H_7$ | H | $n\text{-}C_3H_7$ | $n\text{-}C_3H_7$ |
| 5 | $i\text{-}C_3H_7$ | H | $C_2H_5$ | $C_2H_5$ |
| 6 | $CH_3$ | $CH_3$ | $C_2H_5$ | $C_2H_5$ |
| 7 | $CH_3$ | $CH_3$ | $n\text{-}C_3H_7$ | $n\text{-}C_3H_7$ |
| 8 | $C_2H_5$ | $CH_3$ | $CH_3$ | $CH_3$ |
| 9 | $CH_3$ | $n\text{-}C_3H_7$ | $CH_3$ | $CH_3$ |
| 10 | $CH_3$ | Br | $C_2H_5$ | $C_2H_5$ |
| 11 | $i\text{-}C_3H_7$ | Br | $C_2H_5$ | $C_2H_5$ |
| 12 | $i\text{-}C_3H_7$ | Br | $CH_3$ | $CH_3$ |
| 13 | $sec\text{-}C_4H_9$ | H | $C_2H_5$ | $C_2H_5$ |
| 14 | $sec\text{-}C_4H_9$ | H | $-(CH_2)_5-$ | |
| 15 | $i\text{-}C_3H_7$ | 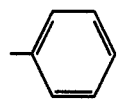 | $C_2H_5$ | $C_2H_5$ |

HERBICIDAL SCREENING TESTS

As previously mentioned, the herein described compounds produced in the above-described manner are phytotoxic compounds which are useful and valuable in controlling various plant species. Selected compounds of this invention were tested as herbicides in the following manner.

Pre-emergence herbicide test.

On the day preceding treatment, seeds of eight different weed species are planted in loamy sand soil in individual rows using one species per row across the width of a flat. The seeds used are green foxtail (FT) (*Setaria viridis*), watergrass (WG) (*Echinochloa crusgalli*), wild oat (WO) (*Avena fatua*), annual morningglory (AMG) (*Ipomoea lacunosa*), velvetleaf (VL) (*Abutilon theophrasti*), Indian mustard (MD) (*Brassica juncea*), curly dock (CD) (*Rumex crispus*), and yellow nutsedge (YNG) (*Cyperus esculentus*). Ample seeds are planted to give about 20 to 40 seedlings per row, after emergence, depending upon the size of the plants.

Using an analytical balance, 600 milligrams (mg) of the compound to be tested are weighed out on a piece of glassine weighing paper. The paper and compound are placed in a 60 milliliter (ml) wide-mouth clear bottle and dissolved in 45 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monolaurate emulsifier to give a final solution of 0.5% (v/v). The solution is then sprayed on a seeded flat on a linear spray table calibrated to deliver 80 gallons per acre (748 L/ha). The application rate is 4 lb/acre (4.48 Kg/ha).

After treatment, the flats are placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

The results of the tests are shown in the following Table II.

TABLE II

Pre-Emergence Herbicidal Activity
Application Rate - 4.48 kg/ha

| Cmpd. No. | FT | WG | WO | AMG | VL | MD | CD | YNG |
|---|---|---|---|---|---|---|---|---|
| 1 | 100 | 90 | 10 | 0 | 60 | 100 | 0 | 0 |
| 2 | 85 | 98 | 0 | 0 | 0 | 0 | 100 | 98 |
| 3 | 100 | 100 | 0 | 0 | 0 | 95 | 90 | 0 |
| 4 | 100 | 100 | 65 | 0 | 0 | 95 | 25 | 0 |
| 5 | 100 | 100 | 60 | 20 | 0 | 95 | 0 | 98 |
| 6 | 70 | 75 | 0 | 0 | 0 | 0 | 0 | 0 |
| 7 | 20 | 60 | 0 | 0 | 0 | 0 | 0 | 0 |
| 8 | 100 | 40 | 0 | 0 | 0 | 90 | 0 | 0 |
| 9 | 90 | 90 | 0 | 10 | 0 | 0 | 0 | 0 |
| 10 | 100 | 100 | 0 | 0 | 0 | 0 | 20 | 0 |
| 11 | 100 | 100 | 0 | 0 | 0 | 30 | 50 | 0 |
| 12 | 80 | 90 | 20 | 0 | 0 | 0 | 0 | 0 |
| 13 | 100 | 100 | 50 | 0 | 25 | 50 | 75 | — |
| 14 | 90 | 100 | 75 | 50 | 20 | 100 | 90 | — |
| 15 | 95 | 95 | 0 | 0 | 0 | 0 | 0 | — |

— = Not tested.

Post-Emergence Herbicide Test.

This test is conducted in an identical manner to the testing procedure for the pre-emergence herbicide test, except the seeds of the eight different weed species are planted 10–12 days before treatment. Also, watering of the treated flats is confined to the soil surface and not to the foliage of the sprouted plants.

The results of the post-emergence herbicide test are reported in Table III.

TABLE III

Post-Emergence Herbicidal Activity
Application Rate - 4.48 kg/ha

| Cmpd. No. | FT | WG | WO | AMG | VL | MD | CD | YNG |
|---|---|---|---|---|---|---|---|---|
| 1 | 10 | 25 | 0 | 20 | — | 60 | 0 | 0 |
| 2 | 0 | 30 | 0 | 15 | — | 20 | 0 | 0 |
| 3 | 100 | 55 | 0 | 20 | 80 | 100 | 0 | 20 |
| 4 | 90 | 80 | 25 | 15 | 100 | 100 | 100 | 15 |
| 5 | 90 | 80 | 25 | 15 | 100 | 100 | 100 | 0 |
| 6 | 0 | 0 | 0 | 40 | 0 | 85 | 0 | 0 |
| 7 | 0 | 0 | 0 | 0 | 40 | 60 | 0 | 0 |
| 8 | 0 | 0 | 0 | 40 | 80 | 100 | 0 | 0 |
| 9 | 35 | 20 | 0 | 40 | 30 | 70 | 0 | 0 |
| 10 | 0 | 20 | 0 | 25 | 0 | 100 | 0 | 0 |
| 11 | 70 | 55 | 0 | 20 | 20 | 20 | 100 | 0 |
| 12 | 70 | 20 | 0 | 45 | 20 | 100 | 0 | 0 |
| 13 | 50 | 60 | 0 | 25 | 50 | 95 | 50 | 50 |
| 14 | 0 | 0 | 0 | 0 | 0 | 50 | 25 | 0 |
| 15 | 25 | 40 | 0 | 0 | 25 | 40 | 65 | 0 |

— = Not tested.

The compounds of the present invention are useful as herbicides, and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for pre-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredients which may include surface-active agents such as wetting agents, dispersing agents or emulsifiers; oil such as heavy aromatic naphthas, kerosene or other petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of powder-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

We claim:

1. A compound having the structural formula

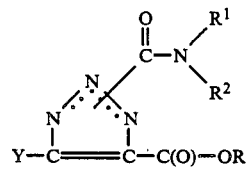

wherein
Y is hydrogen, bromine, phenyl or $C_1$–$C_4$ alkyl;
R is $C_1$–$C_{10}$ alkyl, $R^1$ and $R^2$ independently are $C_1$–$C_6$ alkyl or $R^1$ and $R^2$ together form a ring with the nitrogen to which they are attached having 3–8 carbon atoms, optionally substituted with one or two methyl groups.

2. The compound of claim 1 wherein Y is $C_1$–$C_4$ alkyl, R is $C_3$–$C_6$ alkyl, $R^1$ is $C_1$–$C_4$ alkyl and $R^2$ is $C_1$–$C_4$ alkyl.

3. The compound of claim 1 wherein Y is hydrogen, R is $C_3$–$C_6$ alkyl, $R^1$ is $C_1$–$C_4$ alkyl and $R^2$ is $C_1$–$C_4$ alkyl.

4. The compound of claim 1 wherein Y is bromine, R is $C_3$–$C_6$ alkyl, $R^1$ is $C_1$–$C_4$ alkyl and $R^2$ is $C_1$–$C_4$ alkyl.

5. The compound of claim 1 wherein

Y is $C_1$–$C_4$ alkyl, hydrogen or bromine, R is methyl or isopropyl, or sec-butyl;

$R^1$ is $C_1$–$C_4$ alkyl; and $R^2$ is $C_1$–$C_4$ alkyl or $R^1$ and $R^2$ together form a ring with the nitrogen to which they are attached having 3 to 8 carbon atoms.

6. The compound of claim 1 wherein Y is hydrogen, R is isopropyl, $R^1$ is ethyl and $R^2$ is ethyl.

7. The compound of claim 1 wherein Y is hydrogen, R is isopropyl, $R^1$ is n-butyl and $R^2$ is n-butyl.

8. The compound of claim 1 wherein Y is methyl, R is isopropyl, $R^1$ is methyl and $R^2$ is methyl.

9. The compound of claim 1 wherein Y is bromine, R is methyl or isopropyl, $R^1$ is ethyl and $R^2$ is ethyl.

10. The compound of claim 1 wherein Y is hydrogen, R is secbutyl and $R^1$ and $R^2$ together are pentylene.

11. The method of controlling undesirable vegetation comprising applying to the area where control is desired an herbicidally effective amount of a compound having the structural formula

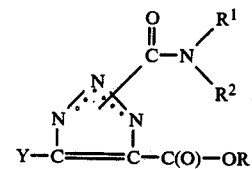

wherein

Y is hydrogen, bromine, phenyl, or $C_1$–$C_4$ alkyl;

R is $C_1$–$C_{10}$ alkyl, $R^1$ and $R^2$ independently are $C_1$–$C_6$ alkyl or $R^1$ and $R^2$ together form a ring with the nitrogen to which they are attached having 3–8 carbon atoms, optionally substituted with one or two methyl groups.

12. The method of claim 11 wherein Y is $C_1$–$C_4$ alkyl, R is $C_3$–$C_6$ alkyl, $R^1$ is $C_1$–$C_4$ alkyl and $R^2$ is $C_1$–$C_4$ alkyl.

13. The method of claim 11 wherein Y is hydrogen, R is $C_3$–$C_6$ alkyl, $R^1$ is $C_1$–$C_4$ alkyl and $R^2$ is $C_1$–$C_4$ alkyl.

14. The method of claim 11 wherein Y is bromine, R is $C_3$–$C_6$ alkyl, $R^1$ is $C_1$–$C_4$ alkyl and $R^2$ is $C_1$–$C_4$ alkyl.

15. The method of claim 11 wherein Y is $C_1$–$C_4$ alkyl, hydrogen or bromine, R is methyl or isopropyl, or sec-butyl; $R^1$ is $C_1$–$C_4$ alkyl; and $R^2$ is $C_1$–$C_4$ alkyl or $R^1$ and $R^2$ together form a ring with the nitrogen to which they are attached having 3 to 8 carbon atoms.

16. The method of claim 11 wherein Y is hydrogen, R is isopropyl, $R^1$ is ethyl and $R^2$ is ethyl.

17. The method of claim 11 wherein Y is hydrogen, R is isopropyl, $R^1$ is n-butyl and $R^2$ is n-butyl.

18. The method of claim 11 wherein Y is methyl, R is isopropyl, $R^1$ is methyl and $R^2$ is methyl.

19. The method of claim 11 wherein Y is bromine, R is methyl or isopropyl, $R^1$ is ethyl and $R^2$ is ethyl.

20. The method of claim 11 wherein Y is hydrogen, R is sec-butyl and $R^1$ and $R^2$ together are pentylene.

* * * * *